United States Patent [19]

Charter

[11] Patent Number: 4,625,553
[45] Date of Patent: Dec. 2, 1986

[54] SYSTEM TO DETERMINE THE LEVEL AND WEIGHT OF LIQUID IN A TANK OR THE LIKE

[75] Inventor: Ian G. Charter, Seabrook, Tex.

[73] Assignee: Dresser Industries, Inc., Dallas, Tex.

[21] Appl. No.: 722,587

[22] Filed: Apr. 12, 1985

[51] Int. Cl.⁴ ............................................. G01N 9/26
[52] U.S. Cl. ..................................................... 73/438
[58] Field of Search ................. 73/715, 714, 706, 299, 73/302, 438

[56] References Cited

U.S. PATENT DOCUMENTS

| | | | |
|---|---|---|---|
| 4,019,387 | 4/1977 | Siegel | 73/299 |
| 4,043,193 | 8/1977 | Bailey | 73/438 |
| 4,111,047 | 9/1978 | Bailey | 73/302 |
| 4,393,878 | 7/1983 | Kahn | 73/715 |

FOREIGN PATENT DOCUMENTS

1355138  5/1984  United Kingdom ................. 73/715

*Primary Examiner*—Stewart J. Levy
*Assistant Examiner*—Robert R. Raevis
*Attorney, Agent, or Firm*—Richard M. Bryon

[57] ABSTRACT

A system for measuring the density of a hydrostatic liquid in a container includes a pair of serially connected pressure sensors mounted in the liquid, a constant volume gas flow source connected to an inlet of one pressure sensor, a second pressure sensor connected to the outlet of the first pressure sensor, and a vent is connected between the second pressure sensor outlet and the atmosphere. A gauge or pressure transducer in the gas conduit from the source to the first pressure sensor provides pressure measurements that can be used to determine the level of liquid in the container and a differential pressure transducer across the first pressure sensor can be used to determine density of the liquid. Exhaust gas from the pressure sensors is passed to the atmosphere through a pressure buffering device in one construction of the system. The pressure sensors each have a rigid body with a generally circular resting surface over which a flexible diaphragm member is positioned. A gas inlet communicates to the peripheral portion of the resting surface through the annular groove. A gas outlet is provided at a central portion of the resting surface for communication with an outlet conduit.

13 Claims, 7 Drawing Figures

SYSTEM TO DETERMINE THE LEVEL AND WEIGHT OF LIQUID IN A TANK OR THE LIKE

TECHNICAL FIELD

This invention is related to fluid level and density measuring systems where submersible pressure sensors are used. In these systems the pressure of a fluid such as liquid acting over a sensor membrane transmits the fluid pressure to gas in the sensor. This gas pressure is monitored so that the relative pressure within a fluid at the location of the pressure sensor can be determined. More specifically, this invention is related to an instrumentation system of pressure sensors for use in oilwell drilling fluid, handling and storage containers operable to monitor the depth and density of drilling fluid in such a container. The specific system of this invention has a pair of serially connected pressure sensors operably connected to a single constant flow gas source with output of the last sensor vented to the atmosphere either directly or through a gas pressure buffering device.

BACKGROUND OF THE INVENTION

This invention is related to hydrostatic fluid pressure and density measuring and monitoring sensors and systems for placement within the confines of a fluid medium such as liquid in a tank to measure depth of liquid in the tank and its density. The specific system of pressure sensors of this invention is in the category of pressure sensors that use a constant gas or air flow through the sensor device and relate the pressure of this gas flow to the hydrostatic pressure of the liquid being measured. The method of operation followed by this system involves passing a constant gas flow through two operably connected and submerged pressure sensors. Input gas pressure to the first sensor is measured along with the pressure differential across the first sensor and this data used in determining liquid level and density. Output from the second pressure sensor is to the atmosphere directly in one embodiment or indirectly in a second embodiment through a third pressure sensor or pressure/flow buffer located above the two pressure sensors.

The broad basic sensing technique of measuring hydrostatic pressures in a liquid to determine depth and density have been used for many years and it provides a quite accurate measurement of hydrostatic pressure. This technique is usable to measure hydrostatic pressure in both liquids and gases. In using this measurement technique several constructions of specific pressure sensor devices have been built for use in specific applications. Depending upon the specific environment in which the pressure sensor is placed and must operate construction of the sensor device will obviously vary considerably. One such prior system is that of U.S. Pat. No. 3,038,336 to M. F. Peters wherein a plurality of bellows type pressure sensors are used to measure depth and density of a liquid. Another multiple pressure sensor system used to monitor a plurality of oil well drilling mud pits is described in U.S. Pat. No. 4,043,193 to J. M. Bailey.

In these and other known prior art systems for measuring liquid depth and density it is common to use two submerged pressure sensors in the liquid container and supply each individually from separate regulated air or gas sources. In using separate air or gas sources for these systems it is quite important that the flow regulation be very precise and constant in order to obtain accurate results and reasonable accuracy of the measurements sought. Testing of this type of system has verified that gas or air flow rate regulation is quite critical for consistently accurate measurements and that even minute variations in the gas flow rate to either pressure sensor will significantly effect the repeatable accuracy of measurements taken with the system.

The specific application of this invention is for measuring the hydrostatic pressure within a container of drilling fluid or mud of the character used with rotary drilling of earth boreholes for oil and gas wells. The mud is basically a mixture of barite, water and other stabilizing elements. A feature of the drilling mud that renders it somewhat difficult to deal with is that it is thixotropic by necessity so that it will support suspended particles of cuttings once the circulation in an earth borehole has stopped. This feature of the drilling mud causes it to cake quite readily when its motion is stopped. This caking will take place not only in the earth borehole while being drilled but in the tanks, containers, etc. for mixing and storing the drilling mud at the earth surface. This caking is accelerated when the mud is exposed to air and it begins to dry.

The pressure sensors used in the monitoring system of this invention are designed to be located in a drilling mud tank with each pressure sensor mounted in a fixed location in the tank. Because of the caking problem, any pressure sensor that is placed in such service will necessarily require periodic cleaning or removal of the mud cake so that it will operate properly and provide data within acceptable limits of accuracy. Because of the necessity for periodic cleaning the structure of this pressure sensor device must be quite rugged in order to withstand its sensing element being brushed, scraped or otherwise wiped clean of the mud cake material. In a drilling mud storage tank the uppermost pressure sensor would be located near the bottom of the tank at a predetermined level to remain submerged as the liquid level varies.

When these pressure sensors require cleaning they would need to be cleaned rather quickly because drilling operations typically proceed in a continuous twenty-four hour operation. Cleaning would be done by raising the sensors above the liquid level manually thus enabling a person to reach into the tank with a brush or scraping device to clean the sensor. It is to be expected that such cleaning would not normally be done in a particularly careful and sensitive manner thus the pressure sensor structures must necessarily be quite rugged in their construction.

One such sensor known to be usable for this type environment is described in U.S. Pat. No. 4,111,047. This sensor construction has a pair of elongated flexible elastomeric membranes that lie in flush contact with each other so that gas can flow between them from one end of the sensor to the other with both membranes being surrounded by the liquid being tested. Pressure acting on the exterior of these flexible elastomeric members transmits liquid pressure in the container to the pressure in the gas. Such a construction is quite susceptible to physical damage when being cleaned due to the unsupported nature of the two members. Another embodiment shown in this patent replaces one of the flexible elastomeric members with a thin flexible metal member. This construction will be slightly more rugged but however it will be subject to damage if the relatively thin metal member is bent or deformed by cleaning or handling.

Another construction known to be used in this type of pressure sensor has a pair of elastomeric membranes with one securely attached to a flat rectangularly shaped side of a support member and a second membrane positioned over the first membrane and sealed around the facing peripheral edge portions with no outer peripheral or edge protection. In this construction ports for gas communication between the membranes are located in a spaced relation on the support member and open through the first membrane that is securely attached to this support member. This permits flow from one port to the other between facing portions of the membranes in the limited area between the two ports. This construction while more rugged than the first described would still be quite vulnerable to damage if the bond between the membranes were to be exposed to brushing or scraping during cleaning. In the event the flexible elastomeric membrane became unbonded it would of course necessitate replacement of the pressure sensor creating an inconvenience and expense in restoring this portion of the drilling mud handling system to its proper operation.

Testing of the prior art devices as described in the paragraph immediately preceding has been done. In this testing a sensor of the described physical construction has been built and tested. In determining the overall accuracy of such instrumentation systems several variables can be controlled because they are known to cause certain variations or inaccuracies in the system's overall performance. One factor that is a major contributor to inaccuracies is variation in the gas flow rate through the sensors. In order to determine the effect of variations in the gas flow rate on the system's performance a test was performed by varying the gas flow rate through one of the two pressure sensors involved from about 0.5 cubic feet per hour to about 1.5 cubic feet per hour through the system at selected flow rate increments while the sensor in a density measuring system is kept at a substantially constant temperature.

During this testing a variation in the liquid density measurements was observed which indicated a rate of change of about 0.68 pounds per gallon per cubic foot per hour, with the actual liquid density being held constant. This represents a measure of the test instrument's ability to provide uniform density measurements as the gas flow increases over a 1 cubic foot per hour flow rate increment. This means that if the gas flow rate through the instrumentation system changes by 1 cubic foot per hour from a selected flow rate the change will cause the density measurements provided by the system to vary by 0.68 pounds per gallon.

This test indicates that the prior art system described would not provide accurate and repeatable measurements if the gas flow rate was to change by 1 cubic foot per hour from a selected flow rate value. In the normal commercial environment for measuring the density of drilling mud it is desirable to keep the accuracy of the measurements to about 0.1 pounds per gallon by this type of density measuring equipment. This accuracy is important so that the overall mix of materials in the drilling fluid can be accurately determined, maintained and modified as needed. Also, it indicates that in order to maintain the accuracy of this system within the nominal 0.1 pounds per gallon accuracy it will be necessary to precisely regulate the gas flow through the pressure sensors to a value that is no greater than 0.1 pounds per gallon divided by the 0.68 pounds per gallon per cubic feet per hour or a variation of 0.147 cubic feet per hour. This amount of regulation is not easily achieved except with sophisticated laboratory grade flow regulating equipment. Furthermore, since the prior art systems each employ two independent constant flow gas sources, each source would need to be held constant to within 0.073 cubic feet per hour for the same permissible density measurement error. The typical flow regulating device that would be used in the oilfield environment is not capable of this degree of accurate flow regulation. Therefore it can be expected that where flow regulating devices are used in the described parallel connected arrangement for density measuring pressure sensors they would not be able to measure the liquid density within an accuracy of 0.1 pounds per gallon. This observation is based on considering the changing gas flow rate parameter alone and neglecting other sources of error that effect the results such as temperature variations and the vertical separation of the pressure sensors relative to one another in the liquid medium.

SUMMARY OF THE INVENTION

One embodiment of the system to determine the level and weight of liquid in a tank of this invention includes a constant flow gas source connected to a first pressure sensor at the lowermost location within a liquid containing tank or the like. The outlet of this first pressure sensor is connected to the inlet of a second pressure sensor at a higher elevation. The outlet of the second pressure sensor is vented to the atmosphere directly. Pressure sensing equipment monitors inlet pressure to the first pressure sensor and a differential pressure between the inlet to the first pressure sensor and the inlet to the second pressure sensor in order to determine the liquid depth in the tank and density of the liquid.

In another embodiment of the system of this invention the constant gas flow source and the pressure sensors are connected as in the first embodiment and a pressure buffering device is incorporated into the outlet flow line from the second pressure sensor. This device buffers or regulates the outlet pressure differential between the second pressure sensor and the atmosphere for the purpose of achieving an improved accuracy of the sensor system over a larger range of liquid depths in the tank.

One embodiment of the hydraulic fluid pressure sensor used in the system of this invention includes a rigid sensor body having a generally circular membrane resting surface with a gas inlet communicating to an outer peripheral annular portion of the resting surface and a gas outlet communicating from a central opening in the resting surface. A flexible membrane lies with one side against the resting surface covering both the inlet groove and the outlet opening. A protective support is mounted around the sensor body for protecting the device and mounting it within a tank or to a supporting structure. Inlet and outlet conduit joining fixtures are provided to connect the sensor in a conduit system.

A second embodiment of the pressure sensors used in the system of this invention is constructed generally similar to the first and has an annular inlet groove in the resting surface around its periphery and a plurality of radially inwardly directed connecting grooves extending toward the centrally disposed outlet opening. The radially disposed groove structure provides a more dispersed generally radially oriented flow of gas between the resting surface and the membrane. This radially grooved structure reduces the restriction to gas flow at the annular inlet port between the radially inner shoulder of the inlet annulus and the space separating the flexible membrane and the rigid body of the sensor.

A third embodiment of the pressure sensor structure usable in the system of this invention is constructed generally similar to the first described embodiment and additionally has an annular outlet. This annular outlet has an annular groove formed in the resting surface generally concentric with the inlet groove and positioned in spaced relation thereto. This outlet groove is connected by a passageway to the sensor gas outlet conduit joining fixture.

One object of this invention is to overcome the aforementioned disadvantages of the prior art liquid and drilling mud pit level and density determining systems.

Another object of this invention is to provide a hydrostatic pressure sensor system for use in a tank or container of drilling mud to provide an accurate measurement of the hydrostatic pressure at a particular depth location, to determine density of the liquid and to have a structural design that will withstand the physical abuse inherent with operation of such a device in this environment.

Another object of this invention is to provide a hydrostatic pressure sensor system having a pair of series connected pressure sensors submerged in the liquid of a tank and connected in a series relation to a constant flow gas source and having the gas output from the second pressure sensor being vented either directly to the atmosphere or indirectly to the atmosphere through a pressure buffering device so the system will provide accurate measurements of liquid depth and density over a wide range of liquid temperatures and depths.

Yet, another object of this invention is to provide a system for measuring drilling mud depth and density using series connected pressure sensors with a common gas supply and series interconnected atmospheric return. In this system each pressure sensor has a generally circular membrane resting surface over which the constant volume source of gas will flow from an annular peripheral location to a centrally disposed location thereby providing uniform dispersion of the gas over an area that is covered with a flexible membrane member. This dispersion of the gas in a uniform pattern over a circular area is important regarding the accuracy of pressure measurements taken in the liquid.

Yet, a further object of this invention is to provide another embodiment of the pressure sensor usable with the monitoring system of this invention with an annular inlet groove around an outer peripheral portion of a membrane resting surface with a plurality of interconnecting radially disposed grooves in said resting surface directed toward the centrally disposed outlet opening. These radially disposed grooves terminate in a spaced relation to the outlet opening and provide a dispersing of gas from the inlet.

An additional object of this invention is to provide a third configuration of pressure sensor that is usable in the liquid level and density monitoring system of this invention similar to the one first described yet being provided with an annular outlet groove in the resting surface as well as the annular inlet groove. This annular outlet groove is concentrically disposed with respect to the annular inlet groove and spaced therefrom.

Yet, another object of this invention is to provide a liquid level and density monitoring system with hydrostatic pressure sensors for use in drilling mud storage tanks or the like that is sufficiently rugged so it can be easily cleaned by a brush, scraper, or similar cleaning instrument with little risk of being damaged by the cleaning operation.

Various other objects, advantages and features of this invention will become apparent to those skilled in the art from the following discussion, taken in conjunction with the accompanying drawings, in which:

The following is a discussion and description of preferred specific embodiments of the hydrostatic head pressure sensor of this invention, such being made with reference to the drawings, whereupon the same reference numerals are used to indicate the same or similar parts and/or structure. It is to be understood that such discussion and description is not to unduly limit the scope of the invention.

DETAILED DESCRIPTION OF THE PREFERRED EMBODIMENT

Figure 1:
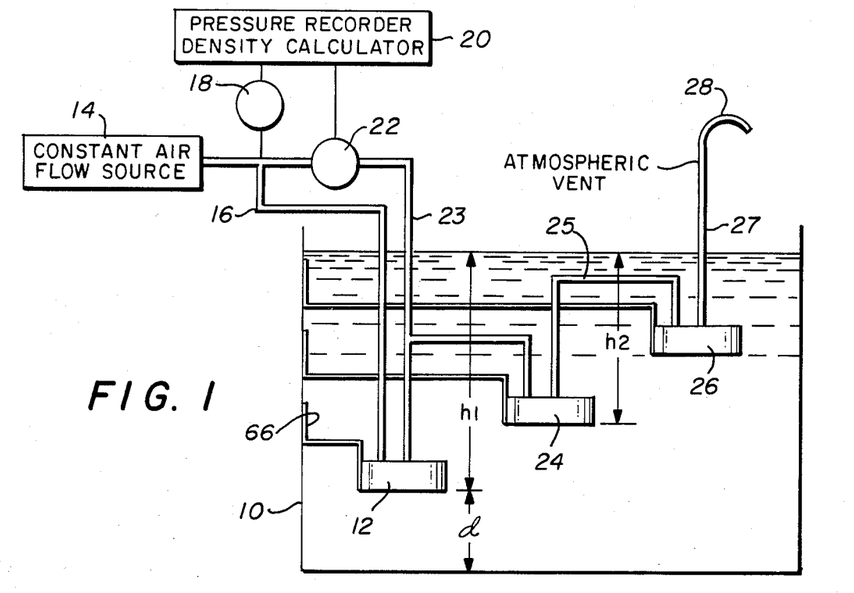
FIG. 1 is a pictorial view of a drilling mud tank having the first embodiment of the liquid level and weight determining system of this invention installed therewith and including a gas flow source, connected in series with the pressure sensors and a pressure buffering device, pressure monitoring equipment and an atmospheric vent located outside of the tank.

Referring to FIG. 1, such shows one embodiment, (1), of the depth and density monitoring system of this invention operably connected for measuring the depth and density of drilling mud in an open top tank. Drilling mud tank 10 contains a quantity of drilling fluid or mud that fills the tank to a level above the hydrostatic head pressure sensors. The lowermost or first pressure sensor 12 has its bottom positioned a distance d above the tank bottom and a distance h1 below the surface of drilling mud in the tank. The gas supply for first pressure sensor 12 includes a constant flow rate air source 14 connected by conduit 16 to the inlet of pressure sensor 12. Air source conduit 16 is connected to a pressure transducer 18 used to monitor the pressure of gas coming from constant air flow source 14. Pressure transducer 18 is operably connected to a pressure recorder and density calculator instrument 20. Connected across first pressure sensor 12 by conduit 23 is an electronic differential pressure transducer 22 that is also operably connected to pressure recorder and density calculator instrument 20 to record the differential pressure across pressure sensor 12 at selected times.

A second pressure sensor 24 has its inlet connected by conduit to the outlet conduit 23 of first pressure sensor 12. First and second pressure sensors 12 and 24 are preferably constructed similarly as described in detail in the following. Second pressure sensor 24 is mounted in tank 10 at an elevation above first pressure sensor 12 and below the expected normal low level elevation of the drilling mud. The outlet of second pressure sensor 24 is connected by conduit 25 to the inlet of a pressure buffering or regulating device 26. This buffering device is in turn connected by conduit 27 to a vent conduit 28 that is in fluid communication with the atmosphere thereby providing an atmospheric pressure return for air leaving the system.

In the event that it is desired to operate the hydrostatic pressure sensor system shown in FIG. 1 in a close top tank or other vessel with pressurized gas above the liquid then the system can be used with equal results. In this application the gas pressure above the liquid would have to be considered as effecting the system. Pressure at pressure transducer 18 would be a differential measurement with respect to the gas pressure in conduit 16 and the gas pressure above the liquid in order to indicate the proper depth. In this modification flow of gas from vent outlet 28 would remain open to the atmosphere outside of the closed tank.

In this discussion of the systems of this invention the gas described in the system is air for purposes of illustration. In actual use of the system other gases such as nitrogen or helium could be used as needed for specific installations.

Figure 3:
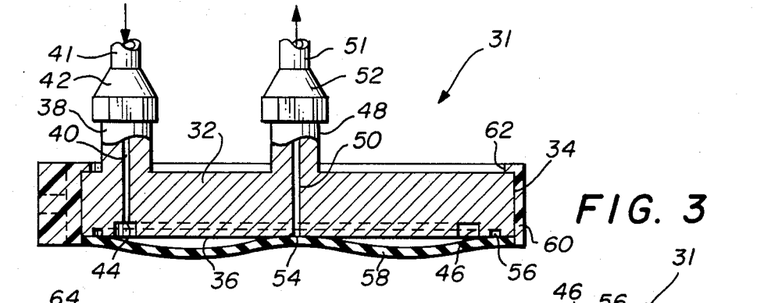
FIG. 3 is a transverse partially cross-sectional view of one embodiment of the pressure sensor usable in the system of this invention having an annular inlet groove and a centrally disposed outlet and shown with the membrane thereof displaced in an operating position.
Figures 4, 5, 6, 7:
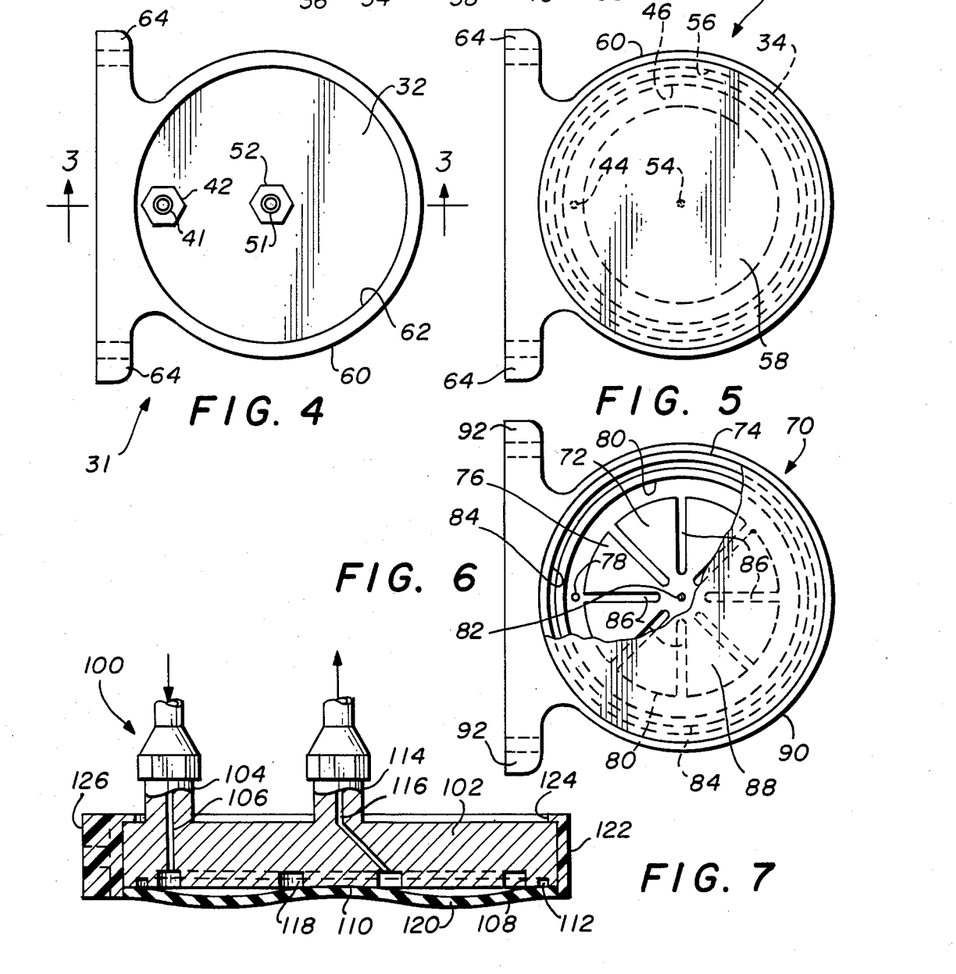
FIG. 4 is a top plan view of the pressure sensor shown in FIG. 3.
FIG. 5 is a bottom plan view of the pressure sensor shown in FIG. 3.
FIG. 6 is a bottom plan view of a second embodiment of pressure sensor usable with the system of this invention having a plurality of radially placed grooves in the resting surface and connected to the annular inlet groove and with the membrane cutaway exposing the resting surface.
FIG. 7 is a partially cutaway view taken in transverse section of another embodiment of pressure sensor usable in the system of this invention having both annular inlet and annular outlet grooves in the resting surface and shown with the membrane thereof displaced in an operating position.

Referring to FIGS. 3, 4, and 5, showing one embodiment (1) of hydrostatic head pressure sensor that is usable with the system of this invention. This specific embodiment (1) of the pressure sensor is indicated at 31 to distinguish it from the following described other two embodiments of pressure sensors shown in FIGS. 6 and 7 because of structural differences in the resting surface for the pressure responsive membrane and associated gas inlets and outlets.

Pressure sensor 31 includes a body 32 with a cylindrical outer surface 34 and a substantially flat membrane resting surface 36 on the bottom side thereof. On the upper side portion of body 32 an inlet fixture 38 is located in relatively close proximity to cylindrical outer surface 34. Inlet fixture 38 contains an inlet passageway 40 opening on its upper end to join an inlet conduit 41 within a fluid coupling 42 and terminating at an outlet opening 44 within the closed end portion of an annular inlet groove 46. Annular inlet groove 46 is located around the outer peripheral portion of resting surface 36 and positioned generally concentrically thereon as shown in FIGS. 3 and 5. Pressure sensor body 32 is preferably constructed of a substantially rigid material that is chemically and mechanically unaffected by the harsh drilling mud materials. Also, pressure sensor body 32 is made of a material that will not stick or adhere to the flexible membrane in the absence of a bonding adhesive applied specifically to secure and seal the two members.

An outlet fixture 48 is located on the upper portion of body 32 and includes an outlet passage 50 therethrough and extending through body 32. Outlet passage 50 is in fluid communication with an outlet conduit 51 joining this conduit at a fluid coupling 52 on outlet fixture 48. The lower end of outlet passage 50 forms the inlet to this passage and such includes an opening 54 centrally located in resting surface 36.

Resting surface 36 is a substantially flat generally circular surface extending across the lower surface of pressure sensor body 32 and being the surface upon which the pressure sensor's membrane will temporarily rest when in a non operating condition and submerged in a liquid such as drilling mud. This resting surface 36 is also the surface that functions as a reference plane for displacement of the flexible membrane as described below.

Membrane resting surface 36 includes an outermost or second annular groove 56 radially spaced outward of annular inlet groove 46 and radially inward of cylindrical outer body surface 34. This second annular groove 56 functions to trap excess bonding material used in attaching the flexible membrane 58 to the outer peripheral portion of resting surface 36. In addition to trapping any excess bonding material this groove also provides a circumferentially disposed limit of flexibility for the membrane 58 so that portions of it lying radially inward of groove 56 can be considered as flexible while portions of it lying radially outside the groove can be considered as attached and sealed. Annular inlet groove 46 is spaced radially inward of second groove 56 and positioned concentrically with respect to outlet opening 54 so that a substantially circular resting surface is provided on which membrane 58 can rest when in a resting or non displaced position.

Flexible membrane 58 is a parallel sided sheet of flexible material that in an undistorted condition lies with one side in flush contact with membrane resting surface 36. Flexible membrane 58 is preferably constructed of an elastomeric type material of sufficient thickness to withstand abuse of the rather harsh environment of the drilling mud holding tank described above. Flexible membrane 58 is preferably constructed of a material that is very flexible and can be substantially unrestrainingly deformed by a relatively low volume gas flow between the inlet and outlet passages across resting surface 36 without significantly restraining this gas flow. The membrane must be made of a material that will not stick or adhere to resting surface 36 during operation of the pressure sensor or at other times when it is not operating. This membrane material must be sufficiently flexible in order to allow hydrostatic liquid pressure acting on the exposed side of the membrane to transmit its force through the membrane into the associated gas flow without unduly restricting the transmission of these forces.

Flexible membrane 58 must be of material sufficiently impervious to gas or air flow and the presence of drilling mud such that it will not absorb or pass either of these fluids but maintain them physically separated. The material from which membrane 58 is made must meet these criteria and additionally have a thermal efficient of expansion that is compatible with the coefficient of expansion of body member 32. Ideally the coefficient of expansion of body member 32 and membrane 58 would be the same. However, if such ideally suitable materials are not available then reasonable compatibility will suffice. Where different coefficients of expansion are involved it is preferable that expansion of body member 32 exceed the expansion of membrane 58. Such a relative expansion condition is preferable in order to prevent the membrane from ballooning away from the sensor body or otherwise being distorted by the gas flow thus disturbing the preferred symmetrical radial flow of gas and the pressure-force relationships involved.

Pressure sensor body 32 is partially enclosed in a mount assembly that protects the sensor and provides a mount structure for securing it in a mud holding tank or the like. This mount includes a support ring portion 60 encircling the cylindrical exterior side of sensor body 32 and having a radially inwardly directed lip 62 overlying the sensor body's top side around the periphery thereof. This mount assembly includes a pair of flanges 64 extending in a tangental fashion from the mounts support ring portion 60 in opposite directions as shown in FIGS. 4 and 5. Each of the flanges has an aperature therethrough for a fastener or bolt to secure the mount to a supporting structure. In FIG. 1 the sensor mount on pressure sensor 12 is shown attached to a mounting frame 66 located in drilling mud tank 10. In this figure the pressure sensors 12, 24 and 26 are shown in a horizontally spaced relation for better illustration. In an actual instrument installation these pressure sensors would be positioned one above the other and have the mounts thereof attached to a single support.

Sensor body 32 is shown as being cylindrical on its outer side 34, however that physical construction is not strictly necessary. If desired sensor body 32 could be rectangular or some other shape on its outer sides and it would function similarly. In such a rectangular construction the body's perimeter would be rectangular and the resting surface 36, inlet groove 46 and other groove 56 would be circular as shown.

FIG. 3 shows pressure sensor 31 in its normal operating position and with membrane 58 in an exaggerated displaced shape illustrating its displaced shape when in use. Displacement of membrane 58 in FIG. 3 is exaggerated to illustrate the general shape of the membrane when in use with gas or air flowing through the sensor. When the sensor is submerged in a liquid such as drilling mud and not in use then membrane 58 is in flush contact with resting surface 36. Membrane 58 is sufficiently flexible that if sensor 31 is not in use and not submerged in a liquid this membrane will drop in an arc like shape across resting surface 36.

FIG. 6 illustrates another embodiment, (2), of a hydrostatic head pressure sensor for use with the system of this invention, indicated generally at 70. This embodiment, (2), of this invention differs from the first described embodiment, (1), in the areas of the construction of the inlet passageways and the grooved construction of the resting surface for the flexible membrane.

In this embodiment, (2), a sensor body 72 is constructed very similar to that described above with an inlet, an outlet, a cylindrical exterior surface 74, and a resting surface 76 on its bottom surface. Sensor body 72 has a substantially flat membrane resting surface 76 on its lower surface extending there across and bounded by outer surface 74. The upper portion of sensor body 72 (not shown) is provided with inlet and outlet fixtures and passageways similar to those in FIGS. 3 and 4 for connection with gas conduits and the like. The gas inlet has a passageway that terminates in an opening 78 lying within an annular groove 80. Annular groove 80 is formed in sensor body 72 around the peripheral portion of resting surface 76. The gas outlet has a passageway through body 72 terminating at an opening 82 located in the center portion of resting surface 76. Outlet opening 82 is centrally disposed relative to annular inlet groove 80. A second and smaller annular groove is provided in resting surface 76 at a location spaced radially outward of annular inlet groove 80. This second annular groove 84 provides a reservoir to collect excess bonding material and to provide a clean line of attachment of the flexible membrane with sensor body 72.

A plurality of radially disposed inlet grooves 86 are provided in resting surface 76 and connected to the inner side of annular inlet groove 80. These radially disposed grooves 86 extend toward outlet opening 82 and terminate a spaced distance therefrom as shown clearly in FIG. 6. Radially disposed grooves 86 are positioned in a substantially uniform and circumferentially spaced relationship to each other and terminate in a similar uniform spaced relation to outlet opening 82. FIG. 6 depicts a quantity of four (4) such radially disposed grooves 86 as exemplifying one arrangement of the inlet groove construction of this invention. It is to be understood that both larger and smaller numbers of these grooves could be used at the designed option of the user. The arrangement of radially disposed spaced apart grooves provides for an even distribution of radially inwardly flowing gas that moves in a manner introducing minimal restriction to the flow at the radially inner shoulder of the annular inlet groove 80.

Flexible membrane 88 is constructed of a sheet of parallel sided flexible elastomeric material the same as that described above so that it will lie flat on resting surface 76 when submerged in drilling mud and be displaceable by the low volume gas flow in order to transmit pressure from the surrounding liquid to the gas during normal operation. Pressure sensor body 72 is enclosed within a protective mount assembly for structural protection and support when in use. This mount includes a support ring portion 90 around the periphery of the sensors outer body surface 74 and overlapping on its upper portion as shown in FIG. 4. The supporting structure of this mount includes a pair of flanges 92 extending from mount ring 90 in a tangental fashion in opposite directions as shown to provide for physical support of the pressure sensor.

FIG. 7 illustrates yet another embodiment, (3), of the hydrostatic head pressure sensor for use with the system of this invention, which is indicated generally at 100. This embodiment of the pressure sensor of this invention is constructed similar to the first described embodiment thereof but differs in the construction of the outlet passageway at the flexible membrane resting surface.

In this embodiment, (3), the sensor body is constructed similar to that described above with inlet and outlet fixtures and associated passageways communicating to a resting surface over which a flexible membrane is positioned. Sensor body 102 is provided with an inlet fixture 104 connectable to an inlet conduit and containing an inlet passageway 106 through the body terminating at an annular inlet groove 108 around the periphery portion of resting surface 110. A second annular groove 112 is provided in the sensor body opening to resting surface 110 and located radially outward of inlet groove 108 to act as a reservoir for excess bonding material.

The pressure sensor outlet includes an outlet fixture 114 that is connectable with an outlet conduit and contains an outlet passageway 116. Outlet passageway 116 extends through pressure sensor body 102 and communicates with an annular outlet passageway groove 118. Outlet annular groove 118 is formed in pressure sensor body 102 opening to resting surface 110 as shown in FIG. 7. Outlet annular groove 118 is positioned in a centrally disposed location with respect to inlet annular groove 108. Inlet annular groove 108 and outlet annular groove 118 are spaced substantially apart so when the sensor is submerged in liquid and not operating flexible membrane 120 will reside on resting surface 110. At this time membrane 120 lies over an annular segment of the surface between these grooves and on the circular segment within the interior of outlet annular groove 118 so long as gas does not flow through the sensor. When the pressure sensor is in operation flexible membrane 120 can be displaced from resting surface 110 causing the gas flow to be substantially radially inwardly directed between inlet groove 108 and outlet groove 118.

Pressure sensor body 102 is partially enclosed in a mount assembly that protects the sensor and provides a mount structure for securing the sensor in a mud holding tank or the like. This mount assembly is constructed similar to those described above and includes a support ring portion 122 encircling the cylindrical exterior portion of sensor body 102 and having a radially inwardly directed lip 124 over the upper peripheral portion of the sensor body as illustrated. A flange assembly 126 includes a pair of flanges located on tangentially opposite sides of the sensor body provided for mounting of the device to a supporting structure. The mount assembly of this embodiment is the same as that shown in FIGS. 4 and 5 in conjunction with the first described embodiment of the pressure sensor.

Referring to FIG. 1, such shows a plurality of pressure sensors connected in one embodiment (1) of the measuring system of this invention with the pressure sensors submerged in a container of liquid. In this instance the container is a tank or the like containing drilling mud. This tank can be a bulk storage tank for drilling mud or a processing container for drilling mud such as the "possum belly" in the mud handling system of a rotary drilling rig. This illustrates one function of the system of this invention. In the system as shown the lowermost pressure sensor 12 and pressure transducer 18 can function to determine the total depth of liquid in the container. The density determining function of this system will be described following the depth determining function.

Measuring the pressure at a selected location in a liquid container for the purpose of determining depth of liquid and the container is well known in the art. In this procedure the following equation is followed:

$P = \rho \times g \times h1$ where:
 P is the measured pressure at the pressure sensor,
 $\rho$ is the density of the liquid,
 g is the gravitational acceleration, and
 h1 is the distance from where the measurement is taken to the surface of liquid.

In this formula the liquid density and gravitational acceleration are known therefore as the pressure is measured the dimension h1 can be calculated.

For the system shown in FIG. 1 its operation is described with lowermost pressure sensor 12 being the specific pressure sensor construction shown in FIGS. 3, 4 and 5. Constant air flow source 14 provides a substantially constant flow of air at a pressure greater than atmospheric pressure to flow through the pressure sensor inlet passage 40 and around and through inlet groove 46. When the flow of this gas displaces membrane 58 from resting surface 36 it assumes the displaced shape as shown in FIG. 3 allowing the gas to flow radially inward in a substantially uniform manner over resting surface 36 and pass into outlet opening 54 in the central portion of the resting surface. Gas flowing toward outlet opening 54 is controlled in its movement by the pressure of liquid acting on the membrane as this pressure is transferred to the gas via the membrane 58. Gas flows from the pressure sensor through conduit 23 and is eventually vented to the atmosphere at vent conduit 28.

Pressure of the liquid is transmitted through membrane 58 into the gas flow and thus is sensed by pressure transducer 18. The gas pressure as monitored by pressure transducer 18 provides pressure data, (P), that can be used to calculate the depth of liquid, (h1), in the tank above the pressure sensor using the above formula. Total liquid depth in the tank is determined by adding the depth of liquid (h1) in the tank above the pressure sensor to the known fixed dimension (d) of pressure sensor 12 from the tank bottom. The gas pressure monitored at pressure transducer 18 is recorded by pressure recorder 20. Pressure recorder 20 can be a device operable to display and record the actual pressure measured, (P), and from that calculate, display, and record the total depth of liquid in the tank, (h1+d), or a tank volume for a tank of known surface area.

Referring again to the complete measuring system shown in FIG. 1, it is assembled and connected to determine the density of liquid in a tank 10. This system includes the constant air flow source 14 connected by conduits to the pair of serially connected pressure sensors 12 and 24, the pressure buffering device 26, and the associated pressure transducers and the recording/calculating instrument 20.

It is well known in the art of measuring devices that two pressure sensors can be used to determine a differential pressure between two separate vertically displaced locations within a liquid and thus determine the density of the liquid. In this art a simple mathematical relationship is used;

$P1 - P2 = \rho \times g \times (h1 - h2)$

Where the terms are as follows:
 P1 is the pressure measured at the inlet to the lower most pressure sensor 12,
 P2 is the pressure measured at the inlet to the second or next higher pressure sensor 24, and
 g is the gravitational acceleration,
 $\rho$ is the density of the liquid,
 h1 is the distance between the surface of the liquid and the location at which the pressure measurement is taken at the first or lower most pressure sensor 12, and
 h2 is the distance between the surface of the liquid and the location at which the pressure measurement is taken by the second pressure sensor 24.

In this equation the density of the liquid, ($\rho$), will be the only unknown term. The differential pressure between P1 and P2 is determined by differential pressure transducer 22. The term (h1−h2) is the known vertical separation of the lower surfaces of the membranes of pressure sensors 12 and 24. Measurements from pressure transducer 22 can be recorded and used for the described calculations by pressure recorder/density calculator 20.

Pressure buffer 26 is placed in the discharge conduit from the second pressure sensor 24 at an elevation above it and at a location that would typically be submerged. This device functions to buffer the outlet pressure from second pressure sensor 24 to an intermediate pressure between the atmospheric pressure and the inlet pressure to second pressure sensor 24 thereby stabilizing the differential pressure relationships of the system. It has been found that this pressure stabilization increases the measuring accuracy of the density measuring system in that the measuring accuracy is not effected by changes in the actual immersion depth of the sensor system beneath the surface of the liquid.

The series connected configuration of the pressure sensors shown in FIG. 1 is an important feature of this invention. Because the constant air flow passes through the two pressure sensors 12 and 24 and the pressure buffering device 26 in a series relationship, thus it assures that the mass flow rate of air utilized by each pressure sensor is the same. The significance of this series connection and equal mass flow rate through the pressure sensors is that it improves operation and measuring accuracy of the system over the prior art systems discussed above.

The series connected pressure sensors of this invention provide temperature compensation by having a continuous flow from the air source through the lower pressure sensor 12 and the upper pressure sensor 24. This temperature compensation relies on the air being influenced by the drilling mud temperature as it passes through conduit 16 to the lower pressure sensor 12 and further in its passage through conduit 23 to the upper pressure sensor 24. Because the air is influenced by the temperature environment its volume is substantially constant as it passes through the pressure sensors with respect to the influence of temperature from its environment of the drilling mud. Ample time is provided for the air to adjust to the mud temperature because the air flow rate in this system can be less than two cubic feet per hour thus moving at a relatively low mass flow rate for proper heat transfer.

For the drilling of wells or earth boreholes the thermal gradient of the earth's crust will greatly influence the temperature of the drilling fluid both in the borehole and the temperature of the fluid as it reaches the earth's surface while being recirculated. These thermal gradients are not constant around the earth but vary in regions of the earth depending on several factors from between about 0.44° F. per hundred foot depth to 2.7° F. per hundred foot depth within the U.S. alone. Within this environment temperature at the bottom of a well bore can reach as high as 680° F. which in turn will heat the drilling mud substantially so that as it reaches the earth's surface the drilling mud can reach a temperature of 190° F. Thus the temperature range over which the system must be able to operate is between an ambient surface temperature that will vary depending upon the wells geographical location and the season of the year and a high temperature of approximately 190° F.

Pressure buffer or regulator 26 is connected by conduit 25 to the outlet of second pressure sensor 24. Pressure buffer 26 is functionally operable as a pressure regulator for the output pressure of second pressure sensor 24. Operationally pressure buffer 26 provides a step in the differential pressure between the pressure of the liquid at pressure sensor 24 and the atmospheric pressure. Because pressure buffer 26 is physically placed at a higher elevation than second pressure sensor 24 and it has a membrane in communication with the fluid to apply the fluid pressure to the air flow at that elevation it will maintain a pressure in conduit 25 that is between atmospheric pressure and pressure of the liquid pressure at pressure sensor 24. If the liquid level in tank 10 drops below the bottom of pressure buffer 26 then it will no longer function to provide a significant step in this pressure differential. However, when such condition occurs second pressure sensor 24 will be at a location that is not substantially below the liquid level in the tank thus removal of this step in the pressure differential for its outlet will not effect the systems operation or accuracy.

Testing of the system shown in FIG. 1 has been done to determine the accuracy with which measurements can be taken by using this instrumentation system. In the testing the system as shown in FIG. 1 was equipped with the pressure sensors as shown in FIG. 3. In determining the overall accuracy of this type of instrumentation system several variables can be controlled that are known to influence variations or inaccuracies in the system's overall performance. One such factor that is known to be a major contributor to such variations is the gas flow rate through the pressure sensors. To determine the effect of variations in the gas flow rate on the system's performance a test was performed by varying the gas flow rate through the series connected pressure sensors of this invention from about 0.5 cubic feet per hour to about 1.5 cubic feet per hour. This variation in flow rate was incremented in several steps over the approximate 1 cubic foot per hour range.

During this testing a variation in measurements taken by the system was observed indicating a rate of change of about 0.08 pounds per gallon per cubic foot per hour. This small change represents the rate of change of the test system's ability to provide uniform density measurements as the gas flow rate changes over an approximate 1 cubic foot per hour flow rate span. In other words, if the gas flow rate through the instrumentation system changes by approximately 1 cubic foot per hour from a selected flow rate it will thus cause the density measurements provided by the system to vary by 0.08 pounds per gallon. It is to be noted that this variation is significantly less than the amount of variation encountered in testing the prior art parallel connected pressure sensors in the system described above.

As mentioned above, the normal commercial environment for this type of system in measuring density of drilling mud requires that the accuracy be kept to about 0.1 pounds per gallon. In view of the test of the system of this invention a variation in the gas flow rate by 1 cubic foot per hour will only produce a variation in the results of 0.08 pounds per gallon which is within the range of acceptable variations.

In normal practice a variation of the gas flow rate of 1 cubic foot per hour from a selected flow rate would be exceptionally large for the average grade of flow regulating equipment that would be used with this type of instrumentation. In order to exceed the 0.1 pounds per gallon this test indicates that the system's gas flow rate must vary more than 1 cubic foot per hour in order for the system's measurements to be outside of the nominal 0.1 pounds per gallon general accuracy requirement. The typical gas flow regulating device that would be used on this equipment in the oilfield environment is capable of regulating the gas flow so the variation in flow rate is significantly and substantially less than 1 cubic foot per hour in variation.

The test described above is based on considering the changing gas flow rate parameter alone and neglecting other sources of error that effect the results and variations in the measurements. Such other sources of error include temperature variations as well as the vertical separation of the pressure sensors relative to one another in the mud tank.

Figure 2:
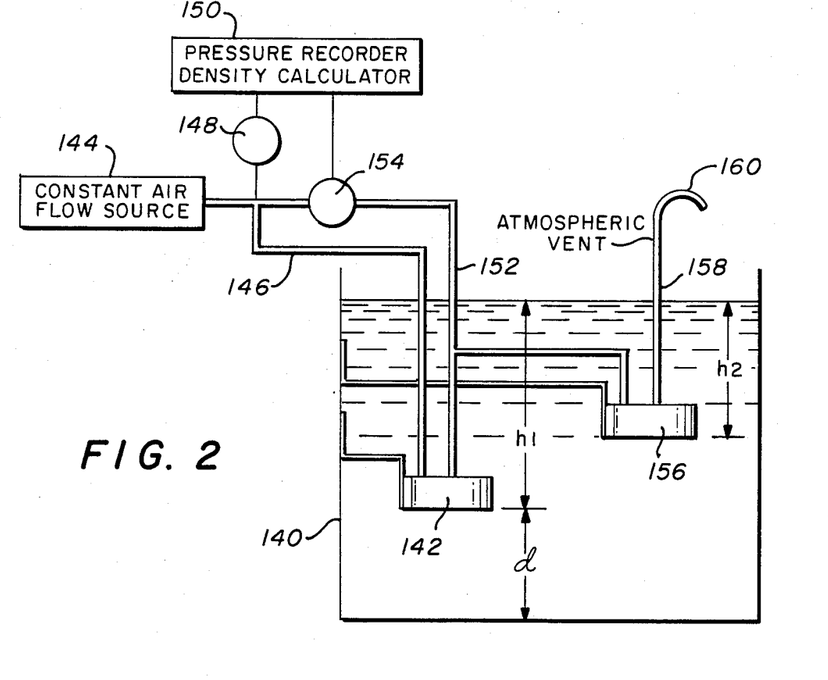
FIG. 2 is a pictorial view of a drilling mud tank having a second embodiment of the liquid level and weight determining system of this invention installed therein and including a constant volume gas flow source connected in series to the pressure sensors the second of which is vented directly to the atmosphere.

Referring to FIG. 2, such shows a second embodiment, (2), of the depth and density monitoring system of this invention in a pictorial manner operably connected for measuring the depth and density of drilling mud in a tank. The drilling mud tank or other similar container 140 holds a quantity of drilling fluid or mud that fills the tank to a level above the uppermost hydrostatic head pressure sensor. In this second embodiment the lowermost or first pressure sensor 142 is positioned a distance at h1 below the surface of the drilling mud in the tank and a distance d above the tank bottom. The gas or air supply for pressure sensor 142 includes a constant flow rate air source 144 connected by a conduit 146 to the inlet of first pressure sensor 142. This air source conduit 146 is connected to a pressure transducer 148 is operably connected to a pressure recorder and the density calculating instrument 150. Pressure recorder and density calculator 150 can display and simultaneously record the measured pressures from the connected transducers and operably derived liquid depth and density parameters.

First pressure sensor 142 is provided with an outlet conduit 152. Connected between or across the inlet and outlet of first pressure sensor 142 is a differential pressure transducer 154 operable to sense a differential pressure in the gas passing through conduits 146 and 152 thereby providing an indication of the differential air pressure across the first pressure sensor. Differential pressure transducer 154 is operably connected to the display and recording device 150. A second pressure sensor 156 is mounted within tank 140 at an elevation above that of first pressure sensor 142. Second pressure sensor 156 has its inlet connected by conduit to the outlet conduit 152 from first pressure sensor 142. The outlet of second pressure sensor 156 is connected by a conduit 158 to an atmospheric vent 160 at a location above the normal highest liquid level of mud tank 140. This atmospheric vent 160 provides a pressure return for the air passing through the system to return to the atmospheric pressure.

In the operation of the liquid depth and density measuring system shown in FIG. 2 it functions the same as that described above in conjunction with the first embodiment of this system except that the exit gas pressure from second pressure sensor 156 is substantially at atmospheric pressure and no buffering or regulating of the discharge air occurs as it returns to atmospheric pressure. The above noted formulas for determining the liquid depth and density apply to this system as well as the first described system.

Because of the serially connected arrangement of the first and second pressure sensors 142 and 156 respectively the system is temperature-volume compensated as described in detail above. This temperature-volume has the effect of substantially increasing the operating accuracy of the system of this invention significantly over prior art devices using separate constant air or gas flow sources for the separate liquid pressure sensors.

With return of the outlet air from this system directly to atmosphere the second embodiment of the system of this invention is structurally simpler than the first described embodiment. The structure of this embodiment can be used in very shallow depth tanks and other containers that have height limitations that would otherwise prevent the use of a system with three submerged devices present in the first described embodiment of this system.

When the system of this invention uses the pressure sensors (shown in FIGS. 3-7) they function substantially the same as in the first embodiment (1) of this invention using pressure sensor 31 described in detail above. Each pressure sensor will accurately transmit liquid pressure from the liquid medium or drilling mud contained in tank to the gas or air as it passes through the pressure sensors thereby providing accurate and responsive data to differential pressure sensor in accordance with this invention.

Also, it is to be noted that pressure sensors other than those shown in FIGS. 3-7 can be used in the system of this invention. In this regard prior art pressure sensors that are substantially functionally equivalent to the pressure sensors shown in FIGS. 3-7 can be substituted in the system of this invention and this will operate to provide an improved measuring accuracy compared to that of prior art measuring systems. Of course the accuracy and total performance of these systems will depend to some extent on the quality, accuracy and general performance of the substitute sensors. However, because of the improved operating characteristics of this invention the systems overall performance will be significantly better than the known and described prior art measuring systems. In using these specific pressure sensors the system shown in FIG. 1 will be improved in its accuracy and performance by the air flow and operating characteristics of these sensor designs as compared to the expected operations with other prior art sensors.

In the use and operation of the several embodiments of the system to determine depth and density of a liquid of this invention it has been found that this system operates to provide an extremely accurate and precise determination of fluid pressures in a liquid medium for a broad range of expected operating temperatures and liquid depths. The construction of the preferred pressure sensors used in these systems is such that they are rugged and are adapted for use in the harsh environment of drilling mud holding and processing tanks. The systems including the pressure sensor are simple in construction and can be duplicated with relative ease from a manufacturing standpoint. The depth and density monitoring system of this invention provides an advancement in the art of such monitoring systems over those used in this environment and service previously due to the sensors are connected and the manner in which the flow of gas through the portion of the sensor functions to expose the gas to pressure of the liquid.

Although specific preferred embodiments of this invention have been described in great detail in the preceding specification this description is not intended to limit the scope of the invention to the particular form or embodiments disclosed herein since they are recognized as illustrative of the invention rather than restrictive and it would be obvious for those skilled in the art that the invention is not so limited.

This invention is declared to cover all changes and modifications of the specific examples and embodiments of the invention herein disclosed for purposes of illustration which does not constitute a departure from the spirit and scope of the invention.

The embodiments of the invention in which an exclusive property or privilege is claimed are defined as follows:

1. A system for measuring the density of liquid in a container, comprising
    (a) a first liquid pressure sensor mounted in a container of liquid and located at a predetermined distance above the bottom of said container, said pressure sensor has a rigid sensor body with a membrane resting surface thereon, a gas inlet communicating to an inlet segment of said resting surface and a gas outlet communicating from an outlet segment on said resting surface, a flexible membrane member is positioned on said resting surface and lies in flush contact therewith in an undistorted state in the absence of gas flow between said inlet and said outlet, and means securing and sealing said flexible membrane to said resting surface to make said membrane responsive to gas flow from said inlet to said outlet in passing between said resting surface and said membrane as influenced by hydraulic liquid pressure acting on the side of said membrane opposite said resting surface,
    (b) a second liquid pressure sensor similar to said first pressure sensor and also mounted in said container at a known elevation above that of said first pressure sensor,
    (c) a constant flow rate gas source connected by a first conduit means to the inlet of said first pressure sensor,
    (d) a second conduit means communicably connecting the outlet of said first pressure sensor to the inlet of said second pressure sensor,
    (e) a third conduit means communicably connecting the outlet of said second pressure sensor to the atmosphere at substantially atmospheric pressure,
    (f) a gas pressure measuring means operably connected to measure the gas pressure at the inlet of said first pressure sensor,
    (g) a differential gas pressure measuring means operably connected to measure the differential gas pressure between the inlet of said first pressure sensor and the inlet of said second pressure sensor, and
    (h) a density calculator means operably connected to said gas pressure measuring means and said differential gas pressure measuring means to determine the depth and density of liquid in the container.

2. The measuring system of claim 1, additionally including:
    (a) an outlet gas pressure buffering means communicably connected in of said third conduit means and positioned at an elevation above said second pressure sensor and including an inlet communicably connected to said second pressure sensor outlet, an outlet communicably connected to the atmosphere via said third conduit means and a liquid pressure communication chamber between said inlet and said outlet and in pressure communication with fluid in the container and said buffering means being operable to reduce the pressure differential across said second pressure sensor.

3. The system of claim 2, wherein said outlet gas pressure buffering means comprises:
    (a) a rigid sensor body having thereon a generally circular and substantially flat membrane resting surface, a gas inlet communicating to a peripheral portion of said resting surface and including a generally annular inlet groove in said body opening to said resting surface,
    (b) a gas outlet communicating with a central portion of said resting surface with an outlet opening in a concentric location relative to said annular groove,
    (c) a flexible membrane member positioned adjacent to said resting surface and lying in flush contact therewith when in an undistorted collapsed state in the absence of gas flow between said inlet and said outlet, and
    (d) means securing and sealing said flexible membrane to said resting surface around the periphery of said generally circular membrane resting surface at a location radially outward of said gas annular inlet groove in order to render said flexible membrane responsive to gas flow along a path from said annular inlet groove between said resting surface and said flexible membrane to said outlet opening and influenced by hydraulic liquid pressure acting on the side of said flexible membrane opposite to said resting surface.

4. The system of claim 1, wherein both of said first and said second pressure sensors are constructed similarly and each comprises:
    (a) a rigid sensor body having thereon a generally circular and substantially flat membrane resting surface, a gas inlet communicating to a peripheral portion of said resting surface and including a generally annular inlet groove in said body opening to said resting surface,
    (b) a gas outlet communicating with a central portion of said resting surface with an outlet opening in a concentric location relative to said annular groove,
    (c) a flexible membrane member positioned adjacent to said resting surface and positioned in flush contact therewith when in an undistorted collapsed state in the absence of gas flow between said inlet and said outlet, and
    (d) means securing and sealing said flexible membrane to said resting surface around the periphery of said generally circular membrane resting surface at a location radially outward of said gas annular inlet groove in order to render said flexible membrane responsive to gas flow along a path from said annular inlet groove and between said resting surface and said membrane to said outlet and influenced by hydraulic liquid pressure acting on the side of said membrane opposite said resting surface.

5. The system of claim 4, wherein said pressure sensors each have:
    a plurality of grooves in said sensor body, each opening to said resting surface and connected to said generally annular inlet groove and extending radially inward therefrom on said circular resting surface toward said outlet opening, said grooves being substantially straight and oriented in a spaced relation to one another and not connected to said outlet opening.

6. The system of claim 1, wherein said pressure sensors each have:
    said outlet including an annular outlet groove in said sensor body opening to a centrally disposed portion of said circular resting surface in concentric relation to said center portion thereof and spaced circumferentially outward thereof and circumferentially inward of said annular inlet groove.

7. A system for measuring the density of liquid in a container that is open to the atmosphere, comprising
   (a) a first liquid pressure sensor mounted in a container of liquid that is open to the atmosphere and located at a predetermined distance above the bottom of said container, said pressure sensor has a rigid sensor body with a membrane resting surface thereon, a gas inlet communicating to an inlet segment of said resting surface and a gas outlet communicating from an outlet segment on said surface, a flexible membrane member is positioned on said resting surface and positioned in flush contact therewith in an undistorted state in the absence of gas flow between said inlet and said outlet, and means securing and sealing said flexible membrane over and around the periphery of said resting surface to make said membrane responsive to gas flow from said inlet to said outlet in passing between said resting surface and said membrane as influenced by hydraulic liquid pressure acting on the side of said membrane opposite said resting surface,
   (b) a second liquid pressure sensor similar to said first pressure sensor and also mounted in said container at a known elevation above that of said first liquid pressure sensor,
   (c) a constant flow rate gas source with an output connected to the inlet of said first pressure sensor,
   (d) said second liquid pressure sensor having its inlet communicably connected to the outlet of said first pressure sensor,
   (e) an outlet gas pressure buffering device mounted in said container at an elevation above said second liquid pressure sensor having its inlet communicably connected to the outlet of said second pressure sensor, and having its outlet communicably connected to an atmospheric pressure vent,
   (f) a differential gas pressure measuring means operably connected to measure the differential pressure between the inlet of said first pressure sensor and the inlet of said second pressure sensor, and
   (g) a density calculator means operably connected to said differential pressure measuring means to determine the density of liquid in the container.

8. The measuring system of claim 7, wherein said first and said second pressure sensors each have,
   (a) said resting surface being generally circular and substantially flat,
   (b) said flexible membrane being bonded around the annular periphery of one side thereof to the facing side of said generally circular resting surface,
   (c) said inlet including an annular inlet groove in said resting surface around a peripheral annular portion thereof in general concentric relation to said gas outlet; and
   (d) said gas outlet having an opening in said resting surface in a centrally disposed location relative to said annular inlet groove.

9. The measuring system of claim 8, wherein said outlet gas pressure buffering device is a third pressure sensor similar to said first and second pressure sensors.

10. The measuring system of claim 9, wherein said pressure sensors are constructed with a body member of a material that is inert and substantially non adhesive with respect to said flexible membrane that is constructed from an elastomeric material.

11. The measuring system of claim 7, wherein said first and said second pressure sensors are each constructed having,
    (a) said resting surface being generally circular and having an annular inlet groove in said sensor body opening to said resting surface around a peripheral portion thereof, and
    (b) a plurality of at least four other grooves connected thereto and equally spaced around said annular inlet groove and extending toward said outlet opening and terminating at a substantially uniform and spaced distance from said outlet opening.

12. The measuring system of claim 7, wherein said first and said second pressure sensors are each constructed having,
    (a) said resting surface being generally circular and having an annular inlet groove in said sensor body opening to said resting surface around a peripheral portion thereof, and
    (b) said gas outlet being an annular outlet groove in said sensor body opening to a centrally disposed portion of said circular resting surface in concentric relation to said center portion of said circular resting surface and spaced circumferentially outward thereof and inward of said annular inlet groove.

13. The measuring system of claim 7 additionally including:
    (a) a gas pressure measuring means operably connected to measure the gas pressure from said constant flow rate gas source at the inlet of said first liquid pressure sensor, and
    (b) said density calculator means operably connected to said gas pressure measuring means and including a depth calculating means operable to calculate the depth of liquid in the container from data of said gas pressure measuring means.

* * * * *